(12) United States Patent
Abraham et al.

(10) Patent No.: US 7,390,641 B2
(45) Date of Patent: Jun. 24, 2008

(54) PRODUCTION OF PEROXIDASE FROM PLANT CELL AND CALLUS CULTURES

(75) Inventors: Tholath Emilia Abraham, Kerala (IN); Nisha Rani Devaki, Kerala (IN); Thomson Kuruvilla, Kerala (IN); Jegan Roy Joseph, Kerala (IN)

(73) Assignee: Council of Scientific and Industrial Research, New Delhi (IN)

( * ) Notice: Subject to any disclaimer, the term of this patent is extended or adjusted under 35 U.S.C. 154(b) by 316 days.

(21) Appl. No.: 11/136,240

(22) Filed: May 24, 2005

(65) Prior Publication Data

US 2006/0021084 A1    Jan. 26, 2006

Related U.S. Application Data

(60) Provisional application No. 60/574,598, filed on May 25, 2004.

(51) Int. Cl.
*C12N 9/08*    (2006.01)
*C12N 5/00*    (2006.01)

(52) U.S. Cl. .................................. 435/192; 435/410

(58) Field of Classification Search ................. None
See application file for complete search history.

(56) References Cited

U.S. PATENT DOCUMENTS 5,728,550 A    3/1998    Fowler et al. .............. 435/70.1

FOREIGN PATENT DOCUMENTS

WO    WO 91/10729    7/1991

OTHER PUBLICATIONS

Usha et al. 2001 Antitubercular Potential of Selected Plant Materials. J. Medicinal and Aromatic Plant Science 22/4A-23/1A: 182-184, abstract.*

N.S. Melo, et al., "Extracellular Peroxidases from Cell Suspension Cultures of *Vaccinium myrthilus*. Purification and Characterization of Two Cationic Enzymes", *Plant Science* (106) 1995; 177-184.

* cited by examiner

*Primary Examiner*—Lisa J Hobbs
(74) *Attorney, Agent, or Firm*—Drinker Biddle & Reath LLP; Daniel A. Monaco, Esq.

(57) ABSTRACT

A process for the production of peroxidase which comprises of establishing a plant cell culture producing cells from neem (*Azardiracta indica*) and nirgundi (*Vitex negundo*) wherein the peroxidase has higher enzymatic activity not reported earlier.

13 Claims, 5 Drawing Sheets

FIG. 3 pH stability of crude Vitex peroxidase

FIG. 4

Optimum temperature of Vitex extracellular peroxidase

FIG. 5

Temperature stability of crude Vitex peroxidase

PRODUCTION OF PEROXIDASE FROM PLANT CELL AND CALLUS CULTURES

FIELD OF INVENTION

The present invention relates to a process for the production of peroxidase, which comprises of establishing a plant cell culture producing cells from neem (*Azardiracta indica*) and nirgundi (*Vitex negundo*) wherein isolated peroxidase has extraordinary higher enzymatic activity.

BACKGROUND INFORMATION

Peroxidase enzymes are widely distributed in nature and are produced by a wide variety of plant species, the chief commercial source being horseradish (*Armoracia rusticana*) and soyabean (*Glycine max*). The horseradish roots are harvested and the sprouted roots are crushed and mixed mechanically with water and a series of ammonium sulphate and ethanol precipitations are carried out for purification. High purity horseradish peroxidase enzyme (HRP) is obtained by conventional chromatographic techniques. But this extraction procedure from the general plant body leads to ecological problems by the dispersal of large quantities of waste and also there is a significant irreversible loss of enzyme activity because of ethanol and ammonium sulphate precipitation (Fowler et al, U.S. Pat. No. 5,728,550). Various other sources have been suggested in the literature for the production of peroxidase. For example, there is a report on the production of peroxidase from the bark of *Hevea brasiliensis* (Phytochemistry, 1997, vol 44, No. 2, pp 237-241); but exact specific activity is not shown. In another report, radish (*Raphanus sativus*) plant cell cultures have been suggested as a commercial source of extra-cellular peroxidase (Plant Cell, Tissue and Organ Culture, 1989, 18:321-327) but the yield and specific activity of the product enzyme are comparatively low.

Several references can be quoted for the use of calli as a source of peroxidase though many of them are of the opinion that callus culture is incapable of large-scale commercial production. Such suggestions are contained in Japanese Patent Applications numbered, JP-A-1222776 (source species: *Trifolium repens L., Carica papaya L., Phellodendron amurense Rupr., Oenothera lamarchiana Ser., Scopolia japonica Maxim, Lithospermum erythrorhizon Sieb et Zucc., Glycine max Merrill,* and *Gynastemma pentaphyllum Makino*; JP-A-63233782 (source species: general); JP-A-1222777 (source species: *Zoysia japonica,* and *Zoysia macrostachchya*); JP-A-62138188 (source species: *Ipomoea aquatica Forsk*); JP-A-1222778 (source species: *Glycyrrhiza glabra L.* var, *Ipomoea batatas Lam. vat deulis Makino, Stevia rebaudiana Bettoni,* and *Bupleurum falcatum L.*).

Reference may be made to *Phytochemistry,* 1998, Vol 49, pp 1219-1225 wherein there is a correlation between plant growth regulators and enzyme activity in cell suspension cultures of *Catharanthus roseus*. Correlation between extra-cellular peroxidase production and plant cell growth has been shown in *Applied Biochemistry and Biotechnology,* 1990, Vol 24/25, pp 213-222 using plant cell cultures of *Artemesia annua, Coleus blumei, Pisum sativum,* and *Salvia officinalis*. In both these cases, no indication is given for its use as a commercial source.

Reference may be made to the International Patent Application, Publication No. WO91/10729, which describes the production of plant cell suspension (root) cultures of *Acer pseudoplatanus* as a convenient source of peroxidase that can be easily recovered. Reference may be made to the U.S. Pat. No. 5,728,550, by Fowler et al 1998, which reports the production of peroxidase from *Acer pseudoplantanus* callus dispersed in liquid culture containing confectionery waste. The drawback is that the enzyme production has not been optimized with growth regulators.

Reference may also be made to the U.S. Pat. No. 59-028473, U.S. Pat. No. 5,70,357, Stepan-Sarkissian et al. 1997, where extracellular peroxidase activity is seen in *Theobroma. cacao* and *Coleus. blumei* and intra-cellular enzyme in *Santalum. alba*. Reference may be made to the two publications titled "Extracellular peroxidases from cell suspension cultures of *Vaccinium myritillus*. Purification and characterization of two cationic enzymes" by Melo et al in *Plant Sciences* 106 (1995) 177-184 and in *Plant Sciences* 122 (1997) 1-10. The drawback is that the specific activity of the enzyme is very low, in the order of 75 U/mg only. Reference may be made to the publication in Plant physiology Biochemistry 39 (2001) 479-486 "Purification and stability of a basic peroxidase from strawberry callus culture". The drawback is that the specific activity is extremely low, 0.56 n Katals/mg, and is not economically viable.

A method for purification of peroxidase by aqueous-organic phase separation is stated by Pokora et al (U.S. Pat. No. 4,992,372). No indication is given for further purification or the specific activity of the purified enzyme.

OBJECTS OF THE INVENTION

The main object of the present invention is to provide novel peroxidase enzyme from *Azadirachta indica* and *Vitex negundo*

Another object of the present invention is to provide a process for the production of peroxidases from plant cell cultures of *Azadirachta indica* and *Vitex negundo*.

Yet another object of the present invention is to provide alternative sources for the commercial extraction of peroxidase enzymes by plant cell culture techniques using locally available and abundant plant resources.

Still another object of the present invention is in choosing better additive and growth regulators for extracellular enzyme production, thus simplifying recovery of the enzyme from the culture medium.

Yet another object of the present invention is to provide a protocol for plant cell cultures of neem (*Azadirachta indica*) and nirgundi (*Vitex negundo*) capable of producing peroxidase enzymes showing exceptionally high levels of peroxidase activity.

Still another object is to provide, in isolated form, novel peroxidase enzymes having activity levels substantially higher than that of HRP.

Still another object of the present invention is the production- of pure enzyme for use in biotransformations and in biosensors.

DETAILED DESCRIPTION

The peroxidase enzyme is extracted from the general plant body or certain parts of the plant like roots. During the isolation of this extract by such process leads to destruction of the plants as well as accumulation of waste materials. Though there are reports about the production of cell suspension cultures for peroxidase production, the present invention provides a unique and novel process to produce compact callus aggregates from unexploited plants and the calluses wherein this protocol shows excellent activity so that they can be reused without much loss of activity. The compact callus aggregates are easy to recover also. The most important part is that in the present invention it has been optimized with the hormone combination and also the combination of the undefined supplement (coconut water) for optimum biomass production and enzyme activity.

Compact callus aggregates showing tremendous enzyme activity were induced so that it could be recovered and reused, whereas the cell suspensions used in earlier studies can not be recovered easily. In most of the commercial preparations, the general plant body is used for the extraction of the enzyme thereby leading to the destruction of the plants as well as accumulation of waste materials. Apart from that, the enzyme purification from the general plant body/microbes is very difficult, and usually nearly 70% price of the purified enzymes may be akin to purification cost.

In the present invention a method was developed by changing the concentrations of hormone combinations and the undefined supplement (coconut water) in order to optimize the biomass growth and enzyme production.

As written earlier, the calluses obtained by the plants show tremendous activity, especially plants of present invention (from these plants peroxidase isolation has not been reported earlier) compared to other known reports. In fact even the crude form of the isolated enzyme from the present invention adds to its feasibility of using for commercial production. Usually, cell suspension cultures are used for enzyme production; whereas we have invoked compact callus aggregates by establishing a protocol which makes recovery and reuse of the enzyme effective.

Impact of growth regulators can alter the enzyme production in a very big way. For example, in the case of *Vitex*, the general plant body as such is devoid of any enzyme activity, whereas its callus shows activity that can be altered by changing the combination and concentration of hormones. A plant regulator is defined by the Environmental Protection Agency as "any substance or mixture of substances intended, through physiological action, to accelerate or retard the rate of growth or maturation, or otherwise alter the behavior of plants or their produce. Additionally, plant regulators are characterized by their low rates of application and higher rates usually followed by decrease in growth rate as most of them function as herbicides. The hormones identified in plants most often regulate division, elongation and differentiation of cells. Plant hormones work in very small concentrations, affecting membrane properties, controlling gene expression, and affecting enzyme activity.

Cytokinins are one of the molecules in DNA. Biologists have yet to identify the genes for the cytokinins found in plants. Parenchyma cells grown in tissue culture will not divide and differentiate unless cytokinins and auxin are present. Cytokinins stimulating RNA and protein synthesis and delaying degradation of chlorophyll. Auxins promote other hormone production. Auxin stimulates cambium cells to divide and secondary xylem to differentiate. In the case of works devoid of hormones, the reason for low enzyme activity may be due to failure of good protocol establishment by adjusting hormone combinations. Moreover, it is not usually possible to establish and maintain callus cultures without using growth regulators.

Specific activity and the yield percentage of both the plants studied are better than all the previous reports we have referred considering its production from both the general plant body as well as callus culture, where very few number of references are available for the latter type. The following Table 1 compares the enzyme activity of our calluses with that of some other plants. (In order to get uniformity, the value using the substrate guaiacol is shown, whereas that using ABTS is still higher for our plants)

TABLE 1

| Plant source | Specific activity | Reference |
| --- | --- | --- |
| *Vaccinium myrtillus* (Bilberry) | 75 U/mg | Melo et al., 1995 |
| *Cichorium intybus* (chicory) | 21.9 U/mg | Bocuf et al., 1999 |
| Straw berry | 0.56 nkat/mg | Arnaldos et al., 2001 |
| *Vitex negundo* | 544 U/mg | Present invention |
| *Azadirachta indica* | 12046 U/mg | Present invention |

As stated earlier, these enzymes evince very good activity which is far better than the commercially available pure enzymes. The compact callus aggregates that have been produced can be reused and can be exploited for continuous production owing to its high activity. Moreover, the commercially available enzymes are extracted from plants like *Armoracia rusticana* (horseradish) that are usually distributed in colder climates only and not commonly available for tropical and other like countries that emphasizes the requirement of an alternative source. The cost of production of these enzymes is very less compared to the cost of commercially available enzymes.

A rough estimate on the cost of enzyme from the plants under study showed that $ 2 was enough for the production of around 2 lakh units of the enzyme whereas it is $450 for the same unit of commercial HRP.

The Compact Callus Aggregates (CCAs) are established using leaf tissues of the plants, *A. indica* and *V. negundo* in full strength Murashige and Scoog (MS) medium augmented with auxins (2,4-dichlorophenoxyacetic acid, naphthalene acetic acid, indole-3-butyric acid) and cytokinins (6-furfuryl amino purine and benzyl amino purine) in different proportions under controlled conditions using sucrose as the carbon source. Suspension cultures of the said calluses are established and maintained using liquid Murashige and Skoog (MS) medium in Erlenmeyer flasks. The production culture can be carried out on a batch basis, semi-continuous or continuous culture techniques with periodic or continuous withdrawal of culture medium and/or cells for recovery of the product, i.e., peroxidase.

In all cases, pH was tried in the range of 5.6 to 6.0 and at a temperature of 23-27° C., albeit the optimum conditions for each species differ. Frequent enzyme assay shows optimum production of peroxidase after about 7 to 15 days. For small-scale experimental work the cultures are sub-cultured by weight, e.g. 3-5 g fresh weight per 100 mL medium. Further scale up cultures can be done by pouring up to two liters of 12-day-old cultures in 10 L of fresh medium in a reaction vessel. Extraction of peroxidase from the culture medium can be done by conventional downstream processing techniques. Concentrated crude extract can be directly used for commercial applications but better activity can be attained by ammonium sulphate or solvent precipitation, dialysis, ultrafiltration, conventional chromatography purification procedures and lyophilization. Intra-cellular peroxidase is recovered by homogenizing the callus in proper buffer followed by purification where as no homogenization was needed in the case of CCA suspension or cell suspension cultures. Extra-cellular peroxidase is recovered by separating the cultured plant cell tissue from the culture medium by centrifugation or ultra filtration and the plant cell tissue left remained can be used to recover intra-cellular peroxidase as a separate product after disrupting plant cells followed by extraction with ethanol and precipitating the extracted intra-cellular peroxidase with ammonium sulphate.

Peroxidase catalyses a host of reactions in which hydrogen peroxide is a specific oxidizing agent and a wide range of substrates act as electron donors.

$$H_2O_2 + XH \rightarrow XOH + H_2O$$

The electron donors used in the assay described in this application are guaiacol, 2,2'-azino-bis(3-ethylbenzthiazoline-6-sulphonic acid) (ABTS) and ortho-Phenylene diamine (o-PDA).

1. Natural Source: *Azardiracta indica*
   Location: Extra-cellular
   Mol. wt: 36 kD
   Optimum pH: 4.5
   Stability: >30% activity retained after 1 year at 4° C. in sodium acetate or
   phosphate buffer
   Haem Peak: λ maximum. 403 nm
   R.Z value: 2.05
   pI: >10
   Highest Specific Activity 12046 U/mg (ABTS):
   Highest Specific Activity 3200 U/mg (Guaiacol):
   Glycosylation: non-glycosylated
2. Natural Source: *Vitex negundo*
   Location: Extra-cellular as well as intracellular
   Mol. wt: 34 kD
   pH range: 3.5-8.5
   Optimum pH: 4.5
   Optimum temperature: 50° C.
   Stability: >80% activity retained even after keeping the crude extract as well as cell suspension supernatant for a period of 6 months at 4° C. in sodium acetate or phosphate buffer
   Haem Peak λ maximum. 409 nm
   R.Z value: 2.10
   Specific Activity: The specific activities shown by using substrates, ABTS, guaiacol and o-PDA were 1572, 544, 3820 respectively under standard assay procedure conditions.
   Highest Specific Activity of crude enzyme: 4864 U/mg (ABTS):
   Inhibitors: $HgCl_2$ ($NaN_3$, $MnSO_4$ and $ZnSO_4$, EDTA and NaCl function as enhancers where as $MgSO_4$ and $CaCl_2$ comparatively imparts no change in activity.)

The specific activities of the crude peroxidase samples from cell culture media or cells were compared to that of a pure sample of horseradish peroxidase purchased from the Sigma Chemical Company, St. Louis, USA (Cat. No. P8375). The protein level has been assayed using the Lowry's assay in exactly the same way as the crude peroxidase samples. The enzyme assay were carried out, using guaiacol, and ABTS as substrates. The results are shown in Table 1.

The *A.indica* enzyme seems to have the highest specific activity with ABTS as substrate, and even in the crude form is substantially more active than the pure horseradish enzyme where as *V.negundo* enzyme shows the highest specific activity with o-PDA as substrate(3820U), and even in the crude form it shows good activity.

Stability studies on freeze-dried samples of the *A.indica* enzymes suggest that the enzyme is very stable at room temperature but for optimum stability may require the addition of stabilizers and cryoprotectants, such as sucrose or trehalose.

The Table 2 shows a comparison between the peroxidases isolated from the prior art and the present invention.

TABLE 2

Comparative chart of neem and nirgundi peroxidases with known horseradish peroxidase of the prior art

| Properties | Horseradish peroxidase (Sigma) | *A. indica* crude | *A. indica* pure | *V. negundo* crude | *V. negundo* pure |
|---|---|---|---|---|---|
| Molecular weight (kDa) | 40 | — | 36 | — | 34 |
| R.Z (Reinheitszahl) value | 2.0 | | 1.9 | | 2.10 |
| pH optimum | 6-7 | 5.0 | 4.5 | 4.5 | 5.5 |
| Optimum temperature(° C.) | 50 | 55 | 50 | 50 | 45 |
| Specific activity (Units/mg of protein): | | | | | |
| Using ABTS: | 1820 | 13406 | 94650 | 1572 | 14730 |
| Using Guaiacol: | 520 | 3200 | | 544 | |

Accordingly, the main embodiment of the present invention relates to the novel peroxidase enzyme from *Azadiracta indica* (Neem) and *Vitex negundo*, said enzymes having the following characteristics:

Natural Source: *Azardiracta indica*
(a) Location: Extra-cellular
(b) Mol. wt: 36 kD
(c) Optimum pH: 4.5
(d) Stability: >30% activity retained after 1 year at 4° C. in sodium acetate or phosphate buffer
(e) Haem Peak: λ maximum. 403 nm
(f) Reinheitszah (RZ) value: 2.05
(g) Isoeletrci point (pI): >10
(h) Highest Specific Activity: 12046 U/mg (ABTS)
(i) Highest Specific Activity: 3200 U/mg (Guaiacol)
(j) Glycosylation: non-glycosylated Natural Source: *Vitex negundo*
(a) Location: Extra-cellular as well as intracellular
(b) Mol. wt: 34 kD
(c) pH range:3.5-8.5
(d) Optimum pH: 4.5
(e) Optimum temperature: 50° C.
(f) Stability: >80% activity retained even after keeping the crude extract as well as cell suspension supernatant for a period of 6 months at 4° C. in sodium acetate or phosphate buffer
(g) Haem Peak λ maximum. 409 nm
(h) Reinheitszah (RZ) value: 2.10

Another embodiment of the present invention relates to a process for the producing peroxidases from plant callus and cell cultures of neem (*Azadiracta indica*) and nirgundi (*Vitex negundo*), said process comprising the steps of:

(a) initiating compact callus aggregates (CCAs) of leaf in solid MS medium or B5 medium,
(b) optimizing growth of CCAs by transferring 5 g FW (Fresh weight) to a 100 ml MS or B5 liquid medium (i.e., medium devoid of agar) containing combination of various growth hormones in the range of about 0.05 to 2 mg/L, a carbon source is about 5% followed by agitation in a gyratory shaker at 120 rpm, (c) sub-culturing of the CCAs of step (b) after every 14 days to fresh media containing optimized growth hormone combination along with coconut water (CW) and different inducers, (d) obtaining maximum extracellular peroxidase produced in the liquid medium from steps (b) and (c) and (e) purifying enzyme peroxidase by ammonium sulfate precipitation by conventional methods.

Still another embodiment of the present invention relates to the cells in the steps (a) to (c) wherein the said cells are cultured under aerobic conditions and at a temperature of about 30° C. and at a pH in the range of about 5-7.

One more embodiment of the present invention relates to the cells in the steps (a) to (c) wherein the said cells are cultured under aerobic conditions and at a temperature of about 25±2° C. and at a pH is in the range of about 5.6-6.

Yet another embodiment of the present invention relates to the inducers wherein the inducers are metals ions selected from group consisting of K, Mg, Na, Zn, Mn, Hg and Ca.

Still another embodiment of the present invention relates growth hormones wherein the growth hormones are selected from group consisting of IAA, NAA, BA, 2,4-D and Kn.

One more embodiment of the present invention relates to the growth hormones wherein the growth hormones are in the range of about 0.1 to 1.5 mg/L.

Yet another embodiment of the present invention relates to the carbon source wherein the carbon source in step (b) is sucrose.

Another embodiment of the present invention relates to the carbon source wherein the carbon source in step (b) is about 2%.

Still another embodiment of the present invention relates to the coconut water wherein the coconut water is about 5%.

Yet another embodiment of the present invention relates to the coconut wherein coconut water is about 1%.

One more embodiment of the present invention relates to ammonium sulfate wherein ammonium sulfate in step (e) is about 60-70%.

Another embodiment of the present invention relates to convention methods of step (e), including ion exchange chromatography and size exclusion chromatography.

Yet another embodiment of the present invention relates to a process of isolating peroxidase from *Azadirachta indica*, said peroxidase having the following characteristics:

(a) Location: Extra-cellular
(b) Mol. wt: 36 kD
(c) Optimum pH: 4.5
(d) Stability: >30% activity retained after 1 year at 4° C. in sodium acetate or phosphate buffer
(e) Haem Peak: λ maximum. 403 nm
(f) Reinheitszah (RZ) R.Z value: 2.05
(g) Isoelectric point (pI): >10
(h) Highest Specific Activity 12046 U/mg (ABTS)
(i) Highest Specific Activity 3200 U/mg (Guaiacol)
(j) Glycosylation: non-glycosylated Still another embodiment of the present invention relates to a process of isolating peroxidase from *Vitex negundo*, said peroxidase having the following characteristics:

(a) Location: Extra-cellular as well as intracellular
(b) Mol. wt: 34 kD
(c) pH range:3.5-8.5

(d) Optimum pH: 4.5
(e) Optimum temperature: 50° C.
(f) Stability: >80% activity retained even after keeping the crude extract as well as cell suspension supernatant for a period of 6 months at 4° C. in sodium acetate or phosphate buffer
(g) Haem Peak .λ maximum. 409 nm
(h) Reinheitszah (RZ) value: 2.10

The following examples are given by way of illustration and therefore should not be construed to limit the scope of the present invention.

EXAMPLES

Example 1

Compact Callus Aggregates (CCAs) are established using leaf tissues of the plants, *A.indica* and *V.negundo* in full strength Murashige and Scoog (MS) medium augmented with auxins (2,4-dichlorophenoxyacetic acid, naphthalene acetic acid, indole-3-butyric acid) and cytokinins (6-furfuryl amino purine and benzyl amino purine) in different proportions under controlled conditions using sucrose as the carbon source. Suspension cultures of the said calluses are established and maintained using liquid Murashige and Skoog (MS) medium in Erlenmeyer flasks. The production culture can be carried out on a batch basis, or with semi-continuous or continuous culture techniques with periodic or continuous withdrawal of culture medium and/or cells for recovery of the product, i.e., peroxidase.

In all cases, pH was tried in the range of 5.6 to 6.0 and at a temperature of 23-27° C., albeit the optimum conditions for each species differ. Frequent enzyme assay shows optimum production of peroxidase after about 7 to 15 days. For small-scale experimental work the cultures are sub-cultured by weight, e.g. 3-5 g fresh weight per 100 mL medium. Further scale up cultures can be done by pouring up to two liters of 12-day-old cultures in 10 L of fresh medium in a reaction vessel. Extraction of peroxidase from the culture medium can be done by conventional downstream processing techniques. Concentrated crude extract can be directly used for commercial applications but better activity can be attained by ammonium sulphate or solvent precipitation, dialysis, ultrafiltration, conventional chromatography purification procedures and lyophilization. Intra-cellular peroxidase is recovered by homogenizing the callus in proper buffer followed by purification, whereas no homogenization was needed in the case of CCA suspension or cell suspension cultures. Extra-cellular peroxidase is recovered by separating the cultured plant cell tissue from the culture medium by centrifugation or ultra filtration. The plant cell tissue left remaining can be used to recover intra-cellular peroxidase as a separate product after disrupting plant cells followed by extraction with ethanol and precipitating the extracted intra-cellular peroxidase with ammonium sulphate.

Peroxidase catalyses a host of reactions in which hydrogen peroxide is a specific oxidizing agent and a wide range of substrates act as electron donors.

$$H_2O_2 + XH \rightarrow XOH + H_2O$$

The electron donors used in the assay described in this application are guaiacol, 2,2'-azino-bis(3-ethylbenzthiazoline-6-sulphonic acid) (ABTS) and ortho-Phenylene diamine (o-PDA).

1. Natural Source: *Azardiracta indica*
    Location: Extra-cellular
    Mol. wt: 36 kD
    Optimum pH: 4.5
    Stability: >30% activity retained after 1 year at 4° C. in sodium acetate or phosphate buffer
    Haem Peak: λ maximum. 403 nm
    R.Z value: 2.05
    pI: >10
    Highest Specific Activity 12046 U/mg (ABTS):
    Highest Specific Activity 3200 U/mg (Guaiacol):
    Glycosylation: non-glycosylated 2. Natural Source: *Vitex negundo*
    Location: Extra-cellular as well as intracellular
    Mol. wt: 34 kD
    pH range: 3.5-8.5
    Optimum pH: 4.5
    Optimum temperature: 50° C.
    Stability: >80% activity retained even after keeping the crude extract as well as cell suspension supernatant for a period of 6 months at 4° C. in sodium acetate or phosphate buffer
    Haem Peak .λ maximum. 409 nm
    R.Z value: 2.10
    Specific Activity: The specific activities shown by using substrates, ABTS, Guaiacol and o-PDA were 1572, 544, 3820 respectively under standard assay procedure conditions.
    Highest Specific Activity of crude enzyme: 4864 U/mg (ABTS):
    Inhibitors: $HgCl_2$ ($NaN_3$, $MnSO_4$ and $ZnSO_4$, EDTA and NaCl function as enhancers where as $MgSO_4$ and $CaCl_2$ comparatively imparts no change in activity.)

The specific activities of the crude peroxidase samples from cell culture media or cells were compared to that of a pure sample of horseradish peroxidase purchased from the Sigma Chemical Company, St. Louis, USA (Cat. No. P8375). The protein level was assayed using the Lowry's assay in exactly the same way as the crude peroxidase samples. The enzyme assay were carried out, using guaiacol, and ABTS as substrates. The results are shown in Table 3.

TABLE 3

Peroxidase specific activities of crude preparations of *A. indica* and *V. negundo* compared with pure *Amoracia rusticana* (horse radish) root peroxidase from Sigma.

| Species | Specific activity (U/mg protein) | |
|---|---|---|
| | ABTS | Guaiacol |
| Pure HRP | 1820 | 520 |
| Crude *A. indica* peroxidase | 3400 | 2200 |
| Crude *Vitex negundo* peroxidase | 1572 | 544 |

The *A.indica* enzyme seems to have the highest specific activity with ABTS as substrate, and even in the crude form is substantially more active than the pure horseradish enzyme, whereas *V.negundo* enzyme shows the highest specific activity with o-PDA as substrate (3820U), and even in the crude form it shows good activity.

Stability studies on freeze-dried samples of the *A.indica* enzymes suggest that the enzyme is very stable at room temperature but for optimum stability may require the addition of stabilizers and cryoprotectants, such as sucrose or trehalose.

Example 3

Production of Peroxidase Enzyme from Neem

1. Initiation and Maintenance of Callus Cultures
    *A.indica* cultures were set up from leaf tissue. The leaf callus was initiated on B5 agar medium containing the hormones 2,4-dichlorophenoxyacetic acid (1 mg/L), and kinetin (0.1 mg/L), with 2% (w/v) sucrose as the carbon source. The pH was adjusted to 5.8 prior to sterilization. From this established suspension line, new cultures were set up by sterile transfer of 20 ml of 10 day culture into 100 ml of fresh medium in 250 ml Erlenmeyer flasks. The flasks are placed on a gyratory shaker at 150 rpm in the light at 25° C. The cultures referred to above were initiated in June 1994 (*A.indica*) and have been routinely sub-cultured since then. Throughout that time the cultures have remained viable and have showed substantially constant levels of peroxidase production.

2. Growth Parameters
    Fresh and dry weight measurements for all the *A.indica* cultures were carried out according to the method described by Stepan-Sarkissian.

3. Estimation of Peroxidase Activity
    In order to determine the percentage contribution of each fraction (cell and medium) to total culture activity, the peroxidase activity was assessed both in the culture medium and in the cell mass. The cells are disrupted on ice using a pre-chilled mortar and pestle with approximately 10% (w/v) pre-chilled, acid-washed sand and ice-cold 0.1M potassium phosphate buffer, pH 7.7. The resulting supernatant is transferred to clean tubes and centrifuged for a further 5 minutes. The supernatant is carefully removed from the centrifuge tube and kept on ice before use.

(a) Guaiacol as Substrate:
    The peroxidase activity of the enzyme was monitored by the oxidation of guaiacol at 470 nm ($\epsilon$ 470=26.6 $mM^{-1}cm^{-1}$). The reaction was performed at 25° C. in 1.3 m reaction mixture containing 60 mM Phosphate buffer (pH 6.1), 1 mM $H_2O_2$, 16 mM substrate and suitable amounts of enzyme. The reaction was started by adding $H_2O_2$ (Shannon et al., 1966). One activity unit (U) is the amount of enzyme yielding 1 µmole of tetraguaiacol per minute under standard conditions.

(b) ABTS as Substrate.
    An aliquot of enzyme solution was added to a solution containing 0.2 g $l^{-1}$ ABTS and 5 mM $H_2O_2$ in 0.05 M acetate buffer, pH 5.0. One ABTS activity unit (U) is the amount of peroxidase that catalyses the oxidation of 1 µmol ABTS ($\epsilon 405-36.8$ $mM^{-1}$ $cm^{-1}$) (Smith et al., 1990)) per minute under standard conditions. The activity was measured by monitoring the absorbance increase at 405 nm.

4. Production of Peroxidase by Cell Cultures
    The production of peroxidase by *A.indica* cultures was monitored using ABTS as a substrate. In all cases productivity peaked at day 11, and the bulk of the activity was found in the medium. The production of peroxidase was greater for glucose-grown cultures 5. Characterization of Crude Peroxidase Preparations
    Peroxidase activity expressed in relation to units of volume of cell culture, or weight of cultured cells, is a useful means of assessing the productivity of a culture system, but to compare the activity of peroxidases from different sources, the specific activity, or activity per mg protein, must be measured. For many commercial uses of peroxidase, particularly those that require the conjugation of the enzyme to a matrix or antibody, the specific activity of the enzyme is the important parameter. Furthermore, purification factor can be measured only by studying the specific activity of an enzyme.

For protein estimations of the crude peroxidase samples, Lowry's test was used.

6. Purification of Peroxidase

Attempts have been made to purify the active peroxidases from the crude enzyme preparations. The primary objective of this was to isolate large enough samples of the various peroxidases to establish whether their properties are superior to the horseradish enzyme in terms of specific activity, stability and useful pH range. A secondary objective was to separate possible isoenzymes and investigate their individual characteristics. The criteria of purity are increased specific activity, appearance of a single band on SDS-PAGE, and the RZ value (the ratio of the haem absorption peak at 403 nm to the protein absorption peak at 280 nm). The RZ value of pure HRP is around 3.0.

An estimate of the protein level was made on the basis of the simple formula of Warburg and Christian i.e., 1.55 times $OD_{280}$ −0.76 times $OD_{260}$=1 mg/ml protein.

HRP was also assessed on the same basis. Even on the most conservative estimation, *A.indica* is considerably more active than pure horseradish peroxidase.

Stability tests: Crude freeze-dried *A.indica* peroxidase has been stored at 37° C. for 2 months without loss of activity. Samples of partially purified enzyme were stored in solution at 4° C. for over a year.

In conclusion, the above data demonstrates that the plant cell cultures of this invention are capable of producing high yields of peroxidase enzymes, all of which show superior properties to horseradish peroxidase, and in particular substantially improved specific activity levels.

Example 4

Production of Peroxidase Enzyme from Nirgundi

1. Initiation and Maintenance of Callus Cultures of Nirgundi (*Vitex negundo*).

Leaf tissues were taken as explants for callus initiation after being properly washed in 10% Labolene followed by surface sterilization in 0.1% Mercuric chloride under aseptic conditions and inoculated in Murashige and Skoog (MS) medium containing 3% sucrose, 0.8% agar in addition to plant growth regulators like kinetin (6-furfuryl amino purine), BAP (benzyl amino purine), 2,4-D (2,4-dichlorophenoxyacetic acid), NAA (naphthalene acetic acid), IBA (indole-3-butyric acid) alone and in different combinations and sub culturing was also done in similar hormone combinations for proliferation. When no hormone was supplied in the medium, callus growth was very slow albeit showing good peroxidase activity. Auxins like IAA/NAA/2,4-D was found to reduce both the callus growth as well as enzyme activity while a cytokinin like BA alone showed better callus growth as well as enzyme activity. 1.5 mg/L BA and 1.0 mg/L 2,4-D was found to be the best combination for getting optimum activity and biomass production. 1% v/v CW (coconut water) was found to be good for better callus proliferation. The pH was kept at 5.8 in all the experiments. Once established, the liquid suspension was maintained by the sub-culturing of 10 ml each of 7 day culture into 100 ml of fresh media in 250 ml Erlenmeyer flasks and the CCAs were also maintained by the subsequent sub-culturing of 5 g each of the sample into fresh liquid media and the flasks were placed on a gyratory shaker at 120 rpm in the light at 25° C. Viability as well as activity was maintained even after a period of 6 months.

2. Growth Parameters

Fresh and dry weight measurements for all the *V.negundo* cultures were carried out according to the method described by Stepan-Sarkissian (1990; U.S. Pat. No. 5,70,357).

3. Estimation of Peroxidase Activity

Both extracellular as well as intracellular enzyme activity was determined in CCAs as well as suspension cultures, respectively. The cells were disrupted on ice using a pre-chilled mortar and pestle with approximately 10% (w/v) pre-chilled, acid-washed sand and ice-cold 0.1M potassium phosphate buffer, pH 7.7. The resulting supernatant was transferred to clean tubes and centrifuged for a further 5 minutes. The supernatant was carefully removed from the centrifuge tube and kept on ice before use.

Peroxidase catalyzes a host of reactions in which hydrogen peroxide is a specific oxidizing agent and a wide range of substrates like phenols and aromatic amines act as electron donors. In addition to ABTS and guaiacol, o-PDA was also used as a substrate.

o-PDA as Substrate:

The assay was carried out in 1 ml cuvettes. Peroxidase activity was assayed with 5 mM of o-PDA and 0.5 mM $H_2O_2$ in citrate buffer (0.1M; pH −4.5). The absorbance increase due to o-PDA oxidation was monitored at 450 nm ($\epsilon$−1.05 $mM^{-1}cm^{-1}$). (Gonzalez et al., 1999)

Enzyme Activity was calculated using the formula, V×($\delta E/\delta t$)/$\epsilon$×d×v µ/ml V—assay volume ($\delta E/\delta t$)—increase in absorbance/min $\epsilon$—extinction coefficient d—path length (1 cm)

v—volume of sample

Specific Activity=Enzyme activity in IU/mg of protein (Protein estimation done by Lowry's method)

4. Production of Peroxidase by Cell Cultures

The production of peroxidase by *V.negundo* cultures was monitored using ABTS as substrate. Optimum activity was shown by the CCAs as well as suspension cultures on the 12th day of inoculation. In both the cases, cytokinins were found to be better for callus growth as well as peroxidase production than the auxins; the best combination being, 1.5 mg/l BA together with 1.0 mg/l 2,4-D.

5. Characterization of Crude Peroxidase Preparations

Measurement of specific activity is the only way of monitoring the purification of an enzyme that can be calculated as total enzyme activity per milligram of protein. Intracellular as well as extracellular activity is shown by *Vitex* callus cultures. A combination of 1.5 mg/L BA and 1.0 mg/L 2,4-D along with 1% v/v CW (coconut water) was found to be the best combination for getting optimum activity and biomass production. Optimum enzyme activity was observed on the 27th day where as maximum biomass was obtained on the 45th day. 1572, 544 and 3820 were the activities of the crude extract using substrates, ABTS, Guaiacol and o-PDA respectively under standard assay procedure conditions. For protein estimations of the crude peroxidase samples, Lowry's test was done using BSA as standard. (Lowry et al.).

Figure 1:
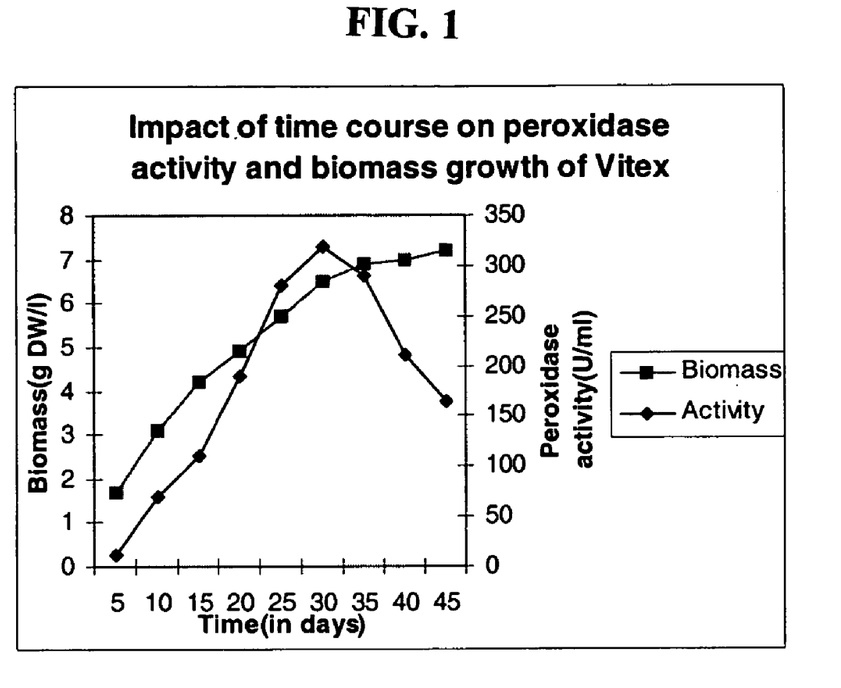
FIG. 1. Impact of the time course on peroxidase activity and biomass growth of vitex FIG. 2. Optimum pH of Vitex extracellular peroxidase FIG. 3. pH stability of crude vitex peroxidase FIG. 4. Optimum temperature of Vitex extracellular peroxidase FIG. 5. Temperature stability of crude vitex peroxidase.

Crude freeze-dried Vitex peroxidase has been stored at 37° C. for 6 months without loss of activity and more than 80% activity was retained by *Vitex* peroxidase even after keeping the crude enzyme (suspension supernatant) for a period of 6 months at 4° C. in sodium acetate or phosphate buffer (FIG. 1).

Figure 2:
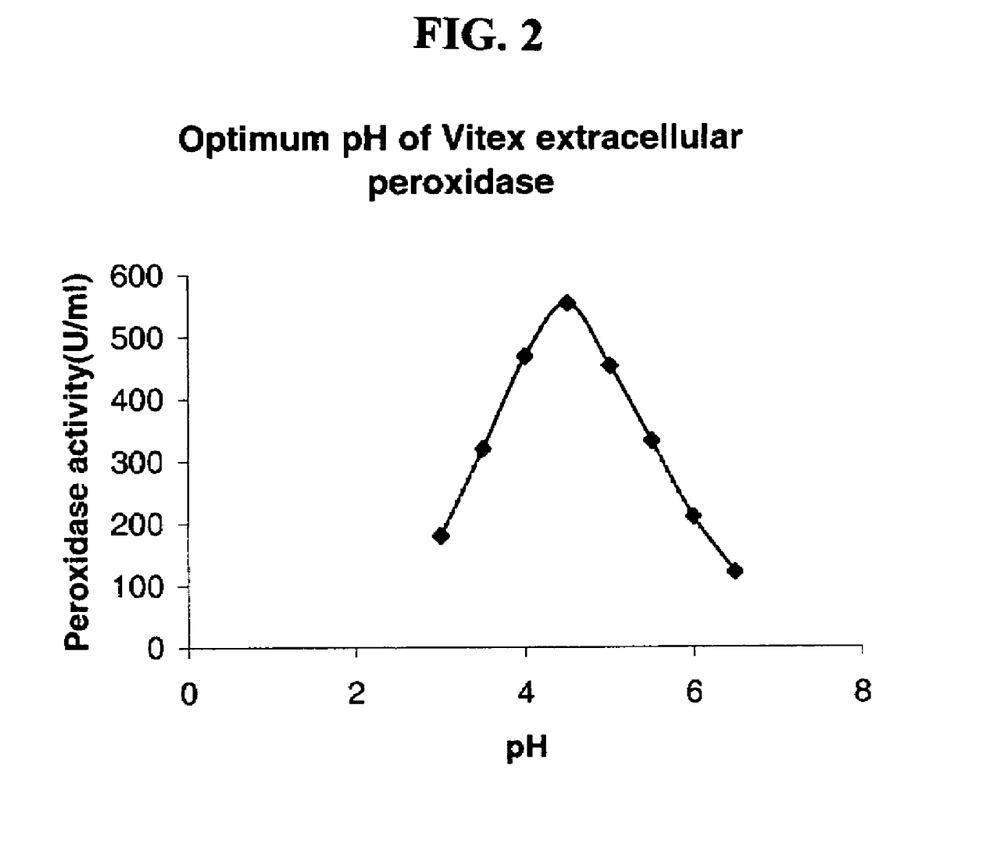
Figure 3:
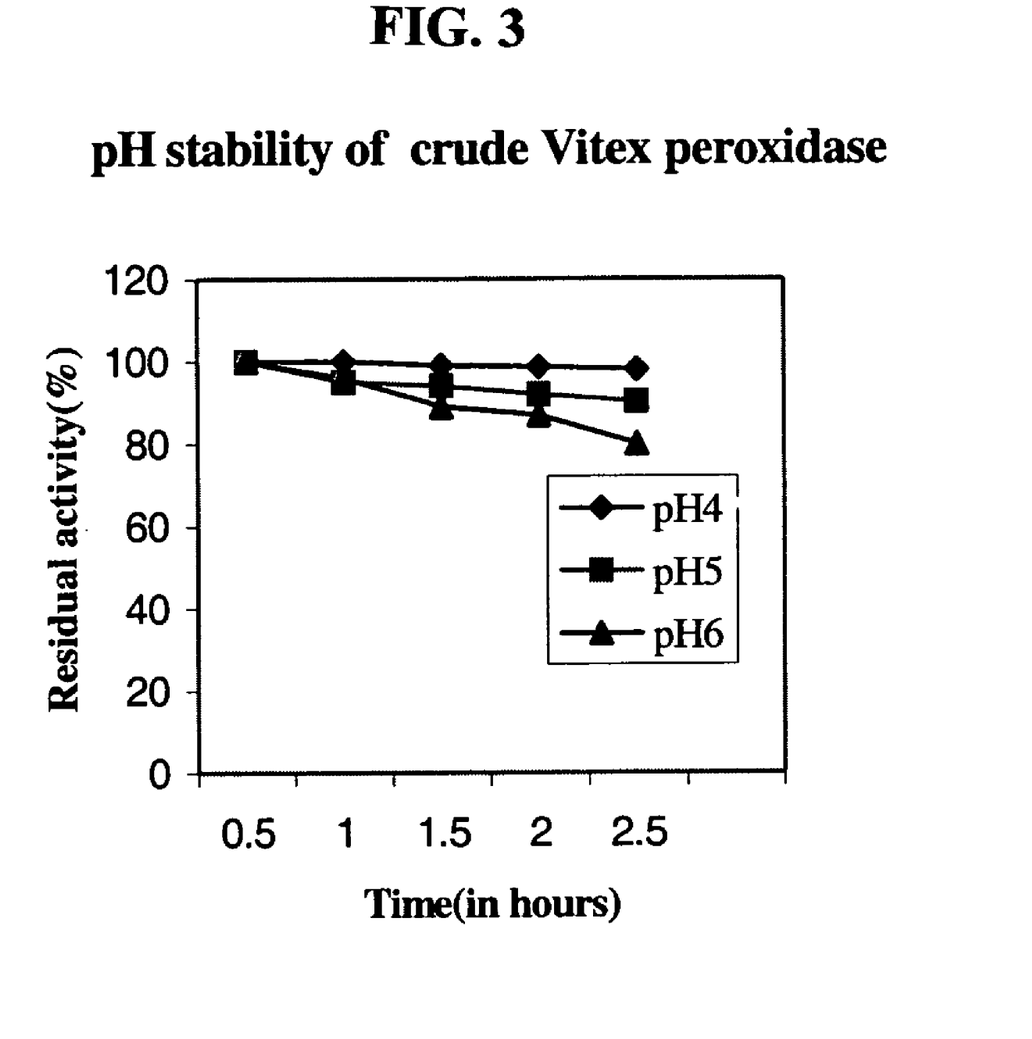

The effect of pH was studied by incubating the enzyme for 30 minutes in buffers having pH ranging from 3.5 to 9.0, and the optimum was found to be at 4.5; along with a pH tolerance of up to 8.5 (FIGS. 2 and 3).

Figure 4:
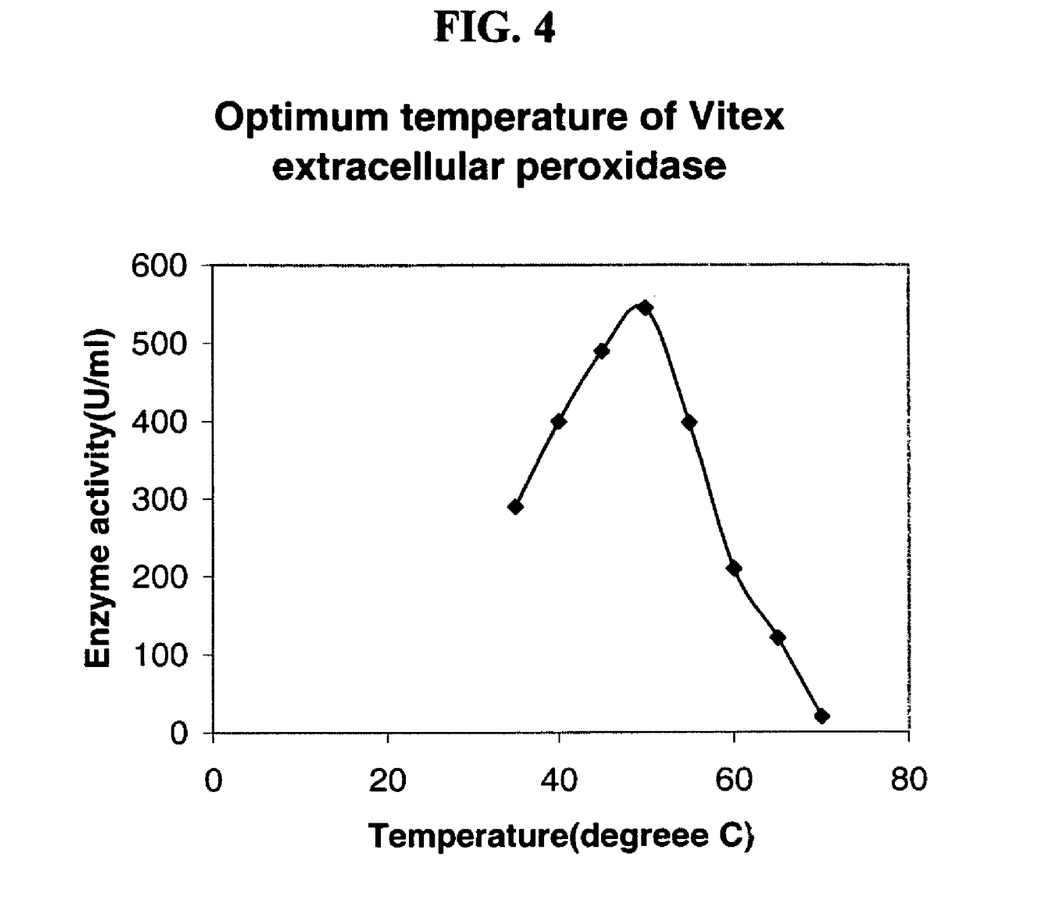
Figure 5:
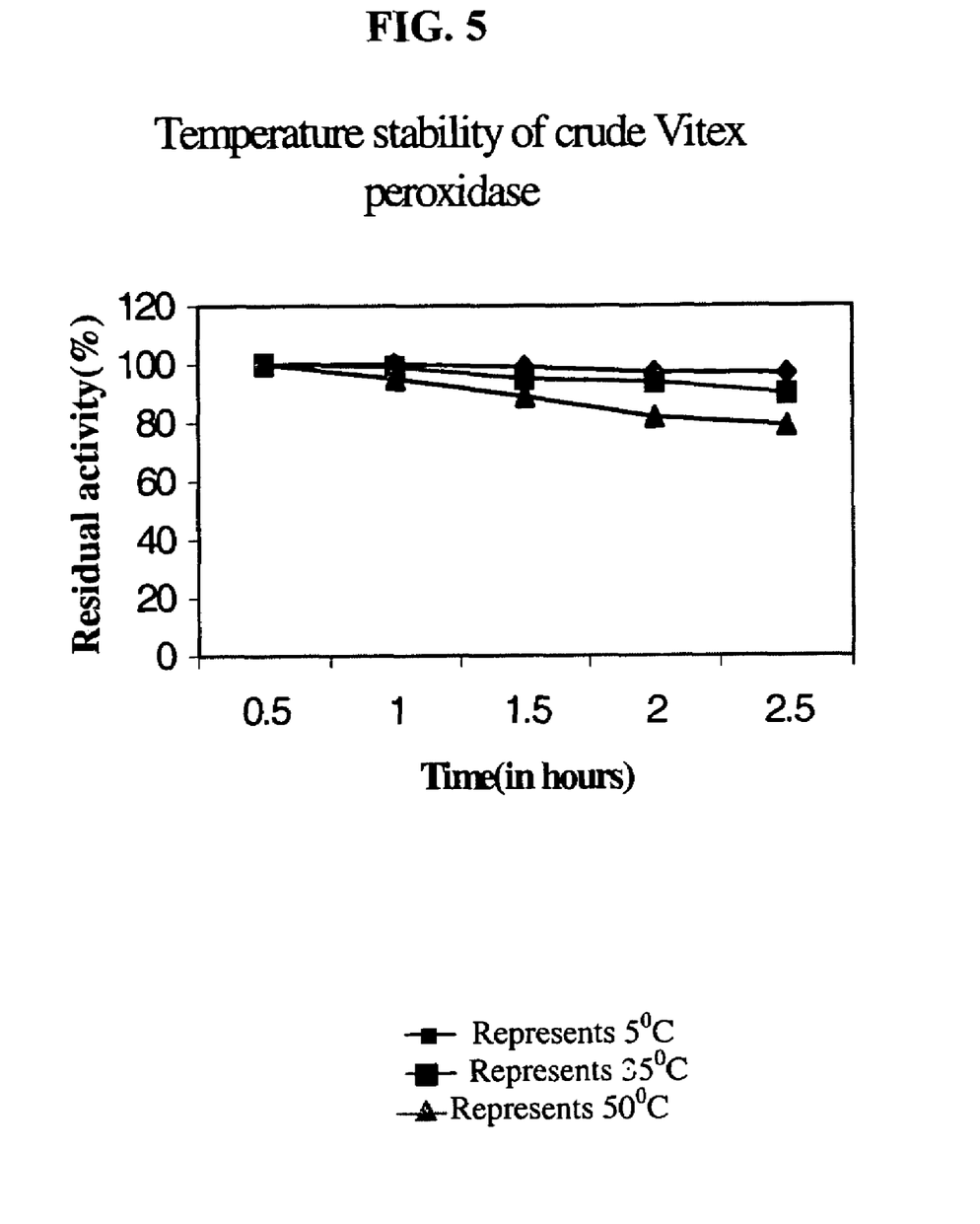

Different temperatures from 35-90° C. were tried to test temperature stability. Enzyme treated at 35-50° C. showed stability, i.e., retained activity even after 1 hour, the optimum being 45° C. From 50° C. onwards, the enzyme showed a decrease in activity and no activity remained after treatment for 1 hour at a temperature more than 65° C. (FIGS. 4 and 5). 0.1 ml of 1 mM sodium azide in 2.4 ml of total assay volume showed 30% inhibition (i.e. 30% reduction in activity.). $HgCl_2$ showed 60% inhibition. $NaN_3$, $MnSO_4$ and $ZnSO_4$, EDTA and NaCl function as enhancers, whereas $MgSO_4$ and $CaCl_2$ comparatively impart no change in activity (Table 4).

TABLE 4

Effects of EDTA and some metal ions on *Vitex* extra cellular peroxidase activity

| No. | Reagent(1 Mm) | Relative activity(%) |
|---|---|---|
| 1 | None | 100 |
| 2 | KI | 116 |
| 3 | $NaN_3$ | 73 |
| 4 | $MgSO_4$ | 97 |
| 5 | $ZnSO_4$ | 138 |
| 6 | $MnSO_4$ | 131 |
| 7 | NaCl | 110 |
| 8 | $HgCl_2$ | 62 |
| 9 | EDTA | 113 |
| 10 | $CaCl_2$ | 103 |

6. Purification of *Vitex* Peroxidase

Crude extract of the callus as well as a suspension was purified by cold centrifugation followed by ammonium sulphate precipitation, after which dialysis was done to remove salt. Ion exchange chromatography and lyophilization were done prior to electrophoresis.

ADVANTAGES

The following are advantages of the invention.
1. Unexplored plants and calluses thereof are utilized to produce peroxidases.
2. The calluses can be reused without much loss of activity.
3. The calluses are easy to recover.
4. The production of peroxidases by the invention is optimized with hormone combination.
5. The process utilizes undefined supplement for optimum biomass production and enzyme activity.
6. The enzyme activity of the obtained enzyme is exceptionally high.
7. The process is extremely cost-effective. $2 is required for the production of about 2 lakh units of enzyme, as compared to $450 for the same unit of commercially available HRP.

We claim:

1. A purified peroxidase enzyme from *Azadirachta indica* (neem) or *Vitex negundo* (nirgundi), said enzyme having the following characteristics:

Natural Source: *Azadirachta indica*;
i. Location: Extra-cellular;
ii. Mol. wt: 36 kD;
iii. Optimum pH: about 4.5;
iv. Stability: >30% activity retained after 1 year at 4° C. in sodium acetate or phosphate buffer;
v. Haem Peak: λ maximum about 403 nm;
vi. Reinheitszah (RZ) value: about 2.05;
vii. Isoelectric point (pI): >10;
viii. Specific Activity: about 12046 to about 94650 U/mg (ABTS); and
ix. Glycosylation: non-glycosylated, or Natural Source: *Vitex negundo*;
i. Location: Extra-cellular as well as intracellular;
ii. Mol. wt: 34 kD;
iii. pH range: 3.5-8.5;
iv. Optimum pH: about 4.5;
v. Optimum temperature: about 50° C.;
vi. Stability: >80% activity retained even after keeping the crude extract as well as cell suspension supernatant for a period of 6 months at 4° C. in sodium acetate or phosphate buffer;
vii. Haem Peak: λ maximum about 409 nm; and
viii. Reinheitszah (RZ) value: about 2.10.

2. A process for purifying a peroxidase according to claim 1 from a compact cell aggregate (CCA) of neem (*Azadirachta indica*) or nirgundi (*Vitex negundo*),
purifying the peroxidase from a liquid culture medium withdrawn from a CCA culture of neem or nirgundi.

3. The process as claimed in claim 2, wherein said CCA culture is under aerobic conditions at a temperature of about 30° C. and at a pH of about 5-7.

4. The process as claimed in claim 2, wherein said CCA culture is under aerobic conditions at a temperature of about 25±2° C. and at a pH of about 5.6-6.

5. The process as claimed in claim 2, wherein said CCA culture comprises a metal ion selected from group consisting of $Kt^±$, $Mg^{2+}$, $Na^±$, $Zn^{2+}$, $Mn^{2+}$, $Hg^{2+}$ and $Ca^{2+}$.

6. The process as claimed in claim 2, wherein said purifying comprises ammonium sulfate precipitation of the peroxidase.

7. The process as claimed in claim 2, wherein said purifying comprises ion exchange chromatography and size exclusion chromatography.

8. The process as claimed in claim 2, wherein said liquid culture medium comprises a hormone that regulates plant cell growth.

9. The process as claimed in claim 8, wherein the growth hormone is selected from group consisting of indole-3-acetic acid, 1-naphthaleneacetic acid, indole-3-butyric acid, 2,4-dichlorophenoxyacetic acid, and 6-furfuryl amino purine.

10. The process as claimed in claim 8, wherein the growth hormone is in the range of about 0.1 to 1.5 mg/L.

11. The process as claimed in claim 2, wherein said liquid culture medium comprises coconut water.

12. The process as claimed in claim 11, wherein the coconut water is at a concentration of about 5%.

13. The process as claimed in claim 12, wherein the coconut water is at a concentration of about 1%.

* * * * *